United States Patent
Reuter et al.

(10) Patent No.: US 6,805,715 B2
(45) Date of Patent: Oct. 19, 2004

(54) METHOD AND DEVICE FOR TREATING INTERVERTEBRAL DISC HERNIATIONS

(75) Inventors: Merrill W. Reuter, Boca Raton, FL (US); Gerald L. Reuter, Plattsburgh, NY (US); Carey D. Rehder, Woodbury, MN (US)

(73) Assignee: PMT Corporation, Chanhassen, MN (US)

( * ) Notice: Subject to any disclaimer, the term of this patent is extended or adjusted under 35 U.S.C. 154(b) by 201 days.

(21) Appl. No.: 10/147,580

(22) Filed: May 16, 2002

(65) Prior Publication Data

US 2003/0069641 A1 Apr. 10, 2003

Related U.S. Application Data

(60) Provisional application No. 60/326,009, filed on Oct. 9, 2001.

(51) Int. Cl.$^7$ .................................................. A61F 2/44
(52) U.S. Cl. ................................................ 623/17.12
(58) Field of Search ........................... 623/17.11–17.16

(56) References Cited

U.S. PATENT DOCUMENTS

| | | | |
|---|---|---|---|
| 4,685,447 A | | 8/1987 | Iversen et al. |
| 5,313,962 A | * | 5/1994 | Obenchain ............... 128/898 |
| 5,888,220 A | * | 3/1999 | Felt et al. .................. 128/898 |
| 5,948,008 A | * | 9/1999 | Daikuzono ................. 99/342 |
| 5,972,015 A | | 10/1999 | Scribner et al. |
| 6,066,154 A | | 5/2000 | Reiley et al. |
| 6,224,630 B1 | | 5/2001 | Bao et al. |
| 6,235,043 B1 | | 5/2001 | Reiley et al. |
| 6,248,110 B1 | | 6/2001 | Reiley et al. |
| 6,280,456 B1 | | 8/2001 | Scribner et al. |
| 2003/0033017 A1 | * | 2/2003 | Lotz et al. ............... 623/17.16 |

* cited by examiner

Primary Examiner—Kevin Shaver
Assistant Examiner—Michael B. Priddy
(74) Attorney, Agent, or Firm—Anthony G. Eggink; Katrina M. Eggink

(57) ABSTRACT

A method and device for treating human intervertebral disc herniations using an endoscopic procedure. An access port is opened into and through the annulus of a disc to remove nucleus pulposus. Laser light fibers may then be passed through an endoscopic guide tube to anneal the inner surface of the disc annulus. Next, a balloon assembly with a valve is placed via the guide tube into the created disc space. The balloon is filled with a fluid to occupy the disc interspace or to maintain some degree of distraction of the created disc space. Post surgery, after fibrocollagenous tissue has grown into the disc space, a second endoscopic procedure is performed to remove the balloon assembly. Fluid is removed to collapse the balloon structure and then removed via the guide tube. The ingrowth of fibrocollagenous tissue will continue to fill the void formerly occupied by the balloon structure. The minimally invasive procedure of the invention allows for short term recovery and early return to normal activity.

35 Claims, 2 Drawing Sheets

METHOD AND DEVICE FOR TREATING INTERVERTEBRAL DISC HERNIATIONS

This application claims the benefit of U.S. Provisional Application No. 60/326,009 filed on Oct. 9, 2001.

BACKGROUND OF THE INVENTION

The present invention relates generally to a method and device for treating intervertebral disc herniations using an endoscopic procedure. Particularly, this invention relates to a distraction disc anthroplasty device and method for treating intervertebral disc herniations. More particularly, the invention relates to a device and method of treating intervertebral disc herniations using a temporary flexible balloon device in the treated disc to alleviate pressure between adjacent vertebrae located in the cervical, thoracic, or lumber areas of the spine.

Intervertebral disc herniations are a major source of back pain. Herniations and ruptures of intervertebral discs may also cause pain and numbness in the leg, feet and arms of affected patients. Herniated, or ruptured, discs may be caused by traumatic injury due to accident, illness, the aging process as well as a multiplicity of undefined causes.

Intervertebral discs are located between adjacent vertebrae of the spine and are comprised of an annulus portion surrounding the nucleus pulposus or pulp. A herniation of an intervertebral disc results from a weakened, torn or stretched area of the annulus. Pulp from the nucleus extrudes through the herniated area in the annulus producing pressure on the spinal column and/or adjacent nerves and thereby causing pain. Removing the pulp reduces pressure on the spinal column or adjacent nerves caused by the herniation.

In the past, intervertebral disc injuries have been treated with implantable disc spacers, for example. These prior art methods typically involve invasive surgery which requires relatively long recovery times for the patient.

It is an object of this invention to produce a minimally invasive interposition arthoplasty procedure which allows for short-term recovery from surgery and the patient's early return to normal activity.

SUMMARY OF THE INVENTION

The present invention relates to method and device for treating a herniated intervertebral disc. The intervertebral disc may be located in the cervical, thoracic or lumbar area of the spine. The method of the invention includes an endoscopic procedure to create an access port in the annulus portion of the herniated or ruptured intervertebral disc. Using a guide tube through the access port, pulp is removed from the nucleus area of the disc. Next, the tissues of the inner surface of the annulus may be annealed to shrink and tighten the annulus so that any ruptured or injured areas can continue the ingrowth process of fibrocartiligenous tissue deposition. A natural or synthetic material may be placed into the disc space in order to promote tissue growth. A balloon assembly having a valve is inserted into the disc space via the endoscopic guide tube. The balloon is then filled with fluid to distract the adjacent vertebrae or to occupy a portion of the intervertebral disc space. The guide tube is then removed from the access port. When fibrocollagenous tissue has grown into the distracted space, usually a few months to a few years, another endoscopic procedure is performed to remove the balloon assembly.

The balloon assembly includes a nubbin or end portion which may be incorporated into the balloon structure to engage and maintain the access port in the disc annulus. The nubbin and/or other portions of the balloon structure may be radiolucent to improve visualization of the balloon assembly during insertion, expansion and removal. The balloon assembly also includes a valve member for filling and deflating the balloon member. Alternatively, the balloon assembly may be constructed of a dissolvable material.

An object of the present invention is to provide a novel method and device of treating intervertebral disc herniations, known as a major source of back pain. The process provides a minimally invasive procedure which allows for short-term recovery from surgery and the patient's early return to normal activity.

Another object of the invention is to improve visualization of the balloon assembly during insertion, expansion and removal from the intervertebral disc space. A further object of the invention is to promote tissue ingrowth in the intervertebral disc space.

These and other benefits of this invention will become clear from the following description by reference to the drawings.

DESCRIPTION OF THE PREFERRED EMBODIMENTS

The present invention relates to a method and device for treating intervertebral disc herniations using endoscopic procedure. The method provides a minimally invasive procedure which allows for short-term recovery from surgery and a patient's early return to normal activity.

Figure 1:
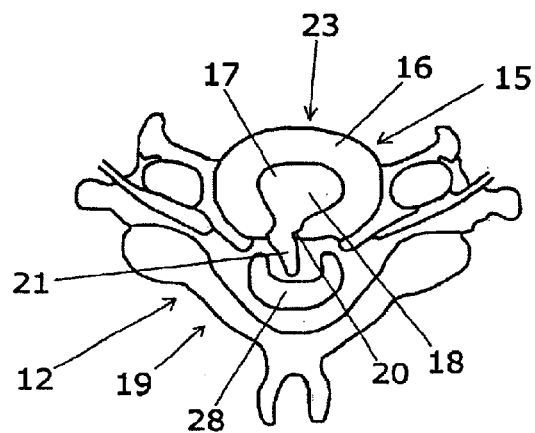
FIG. 1 is a top sectional view showing a ruptured intervertebral disc.

FIG. 1 shows a top sectional view of a herniated disc 15 of a spine 12. Spine 12 is shown to have a vertebral canal 28 and having posterior region 19 and anterior area 23. Disc 15 is shown having annulus portion 16 surrounding nucleus portion 17. Nucleus portion 17 is made up of pulp 18. The disc 15 is shown to be herniated or ruptured at herniation 20, whereby pulp 21 is shown extruding from nucleus 17 and through annulus 16 into the posterior region 19 of the spine thereby causing pain to the patient. The expressed or extruded pulp 21 from the disc space may be an irritant to nerve tissue that lie posterior to the vertebral column and may be a cause of back pain. It may also be the cause of referred pain and numbness to affected arm, hand, leg or foot areas.

Figure 2:
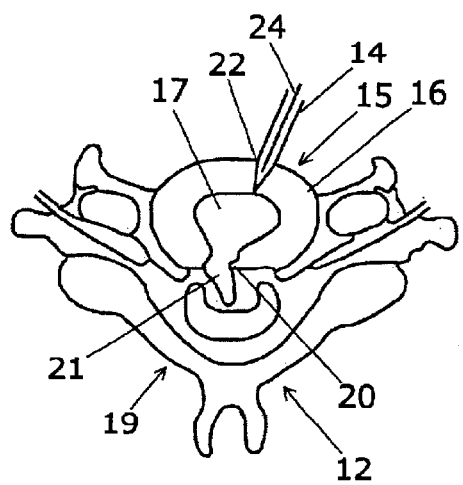
FIG. 2 is a top sectional view showing a guide tube advanced through the access port in the anterior of the disc annulus.
Figure 3:
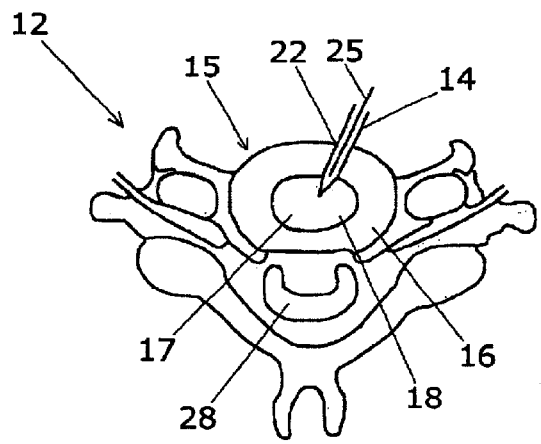
FIG. 3 is a top sectional view showing the pulp removed from the disc.

The endoscopic procedure initially involves a surgical skin incision of approximately 3 mm in the skin and through which an endoscopic guide tube 14 is passed. FIG. 2 shows guide tube 14 inserted into disc 15 through annulus 16 and into nucleus 17. Trocar 24 is inserted within the guide tube 14 and is used to aide in forming access port 22 so that extruded pulp 21 may be removed. FIG. 3 shows pulp 18 being removed from the disc interspace through guide tube 14. The guide tube 14 is preferably a long radiolucent needle-like probe having an internal diameter of about 2.5 millimeters. The guide tube 14 is manually guided by imaging technique to the proposed entry or access port 22 to be created in the targeted annulus. The access port 22 then allows for removal of the nucleus pulposus. Disc removal instrument or grasper 25 is shown within the guide tube 14 to remove the pulp 18.

The annulus 16 may next be laser annealed to cause shrinking and tightening of the tissues of the annulus 16 to reduce the size of any lateral or posterior tears in the annulus from which nucleus pulposus 18 may have expressed out from the intervertebral disc space.

Figure 4:
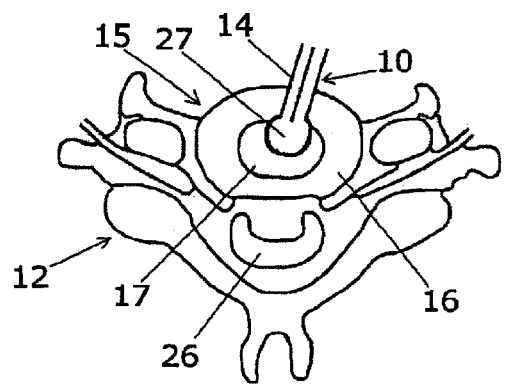
FIG. 4 is a top sectional view showing the balloon assembly expanded by a fluid.
Figure 5:
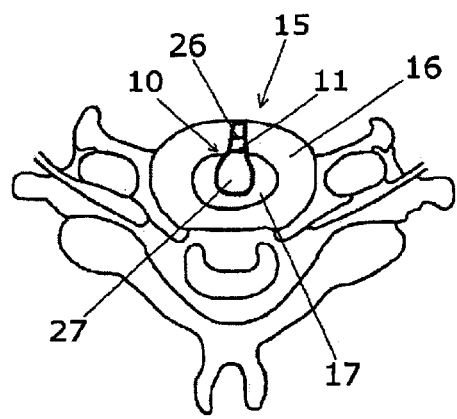
FIG. 5 is a top sectional view showing the filled balloon structure and the instrumentation removed.
Figure 6:
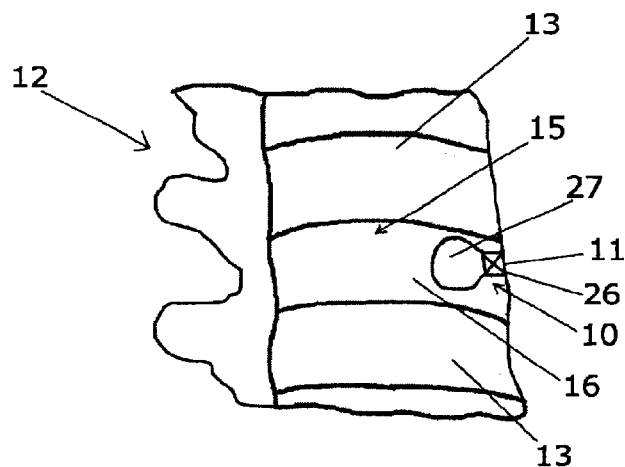
FIG. 6 is a lateral sectional side view showing the filled balloon maintaining distraction of the adjacent vertebrae.

FIG. 4 shows balloon assembly 10 being inserted through guide tube 14 and into nucleus 17. Expandable balloon structure 27 is shown within the disc 15 of spine 12. FIGS. 5 and 6 show balloon assembly 10 secured in disc 15 with the guide tube and instrumentation removed through the incision. Disc 15 is shown positioned between vertebrae 13 of spine 12. The nubbin or end portion 11 of balloon assembly 10 is shown secured in the annulus 16. Balloon assembly 10 is shown having valve 26 in nubbin 11 and an expandable balloon structure 27.

The nubbin 11 or other portions of the entire balloon assembly 10 may be radiolucent in order to make it easier to locate during the endoscopic procedures. Alternatively, the balloon assembly 10 may have radiolucent markers added thereto for purposes of locating and maneuvering the assembly 10 during the process steps of the invention. Further, the balloon structure may utilize silicone pigments or expansion fluid which is radiolucent. The balloon assembly 10 is also preferably constructed of MRI and CT compatible materials. A physiologically compatible fluid such as physiological normal saline or the like is preferably used to fill the balloon via the valve. The filled balloon distracts the adjacent vertebrae 13 thereby providing structure in the void or space formerly filled with the removed pulp. The filled balloon may also occupy the intervertebral disc space after the pulp has been removed, whereby the space is substantially occupied.

It is within the purview of this invention to utilize a balloon assembly constructed of a dissolvable material composition. The utilization of a dissolvable balloon structure, which preferably would dissolve in a specified time period, would alleviate the need of the subsequent removal of the balloon assembly from the patient.

Prior to the placement of the balloon, a medically suitable option such as powdered hydroxyapatite or cell culture material or the like to facilitate the ingrowth of structured tissue in the intervertebral space formerly occupied by the removed pulp may be used. Homologous tissue cell culture seeding may also be used to facilitate the ingrowth of structured tissue in the distracted space.

After removing the endoscopic instruments the approximately 3 millimeter skin incision is closed by suture, staple, bonding agent, adhesive bandage, or like procedure.

After about 1 month to about 3 years, when fibrocollagenous tissue has grown into the intervertebral disc space, a second endoscopic procedure is performed to remove the balloon assembly 10. In this endoscopic procedure the fluid is removed from the balloon structure and the balloon is then removed via the guide tube 14 and through the port in the annulus that the nubbin has kept patent or open. An imaging technique facilitates guiding the endoscopic guide tube to the radiolucent nubbin.

Finally, after all endoscopic instruments are removed, suture, bonding agent, adhesive bandage or like procedure is used to close the skin incision.

The procedure of the invention employs a minimally invasive endoscopic procedure which provides for a reduced cost, less time involved surgical procedure, and a patient's short term surgical recovery and early return to normal activity. The procedure can be performed at all areas of the spine, including cervical, thoracic and lumbar areas.

A more detailed description of the procedure as applied to an anterior cervical discectomy is as follows:

The procedure of this invention may be performed in an outpatient surgical setting. The patient is initially placed under general endotracheal anesthesia and wired for intaoperative electromyography and somatic evoked potential spinal monitoring. Dexamethasone and a prophylactic antibiotic are administered by intravenous route. The patient is positioned supine with gentle cervical extension. A Phillips standard operative fluoroscopy C-arm or the like is adjusted to confirm imaging in both anterior-posterior and lateral projections. The anterior neck is surgically prepared and draped in sterile fashion. Under fluoroscopic guidance and with digital pressure retracting the carotid sheath the affected disc level is identified. The overlying skin is anesthetized with Marcaine 0.25% with epinephrine or the like.

A short transverse incision is made in the anterior neck region anterior to the sternocleidomastoid muscle while holding retraction on the carotid sheath and providing a safe interval between the paratracheal and carotid sheath structures. The incision is then bluntly dissected to allow for placement of the discogram needle into the safe interval. Utilizing digital pressure a trochar is then placed down into the anterolateral aspect of the intended disc. Anterior-posterior and lateral radiographs confirm the position. The discogram needle is then placed into the central portion of the disc with position again confirmed by fluoroscopy. Lopamidol 51%, or other suitable contrast agent may be added in a mixture with lidocaine 1% without epinephrine is instilled into the interspace. This step is performed to identify any epidural leaks and marking of the disc to assist with directing and assessing the disc removal.

Next, the hub of the discogram needle is removed and a 2.5 millimeter dilator is placed over the needle/trocar. This process step is monitored under fluoroscopic guidance down to the anterolateral aspect of the annulus. The cannula and the dilator are both replaced seating the cannula on the anterior annulus. The 2.5 millimeter trephine is then inserted into the interspace under fluoroscopic guidance providing an anterior anulotomy. The trephine and trochar are then removed. The 2.5 millimeter disc removal instrument is placed into the central region of the disc and the position confirmed with fluoroscopy. The 2.5 millimeter grasper is then employed to remove the trephine annular core if the disc removal instrument did not evacuate it. Irrigation and aspiration of the disc with resection is then commenced with approximately 1 to 3 cubic centimeters of disc material collected in about 20 to 30 minutes of combined aspiration and cutting. The discectomy is focused in the posterior region of the interspace in the area of the predominant disc herniation. Once a quantitative amount of contrast agent and disc material is removed the graspers are used to remove any free fragments.

Following the latter step the flexible LASE endoscope by Claris Medical Systems, Inc., Minneapolis, Minn., U.S.A., or the like is then placed into the interspace with the position confirmed by fluoroscopy and direct vision. Using direct vision, laser discoplasty is accomplished with 800 to 1500 kilojoules using holmium laser by New Star Lasers, Roseville, Calif., U.S.A. or the like. Under endoscopic visualization the posterior annulus fibers are identified and treated. Additional laser modulation in the uncinate regions further stabilizes the segment and decreases discogenic neuroforaminal encroachment.

Under fluoroscopic guidance, the balloon assembly is then inserted into the anterior aspect of the interspace and then inflated. Spinal monitoring is utilized continuously introperatively to confirm satisfactory response and no neurologic changes. The balloon device position is then confirmed by direct endoscopic and fluoroscopic evaluation. The interspace is irrigated and the instruments are removed.

The skin incision is cleansed with a physiologically normal saline soaked sponge and approximated with a 4.0 ethilon stitch while maintaining pressure to minimize bleeding. A Philadelphia firm collar or like cervical collar is then placed onto the patient. The patient is then extubated and leaves the operating room awake and in the care of an anesthesiologist. After about 3 hours of post surgical monitoring the patient is released to limited home activity.

While the above described procedure offers patients an additional 5 or 10 years or more without spinal fusion, this procedure, employing the distracted disc arthroplasty device, not only lessens the stresses on adjacent vertebral disc segments but leaves open the possibility of procedure to place a functional prosthetic device that may very likely appear in the near future.

After about a few weeks to about a few years post surgery when fibrocollagenous tissue has grown into the distracted space another endoscopic procedure is performed to remove the balloon device. This second procedure removes fluid from the balloon device to deflate the device for removal via the access port in the annulus. Again, after the endoscopic instruments are removed, the skin incision is closed as previously described. The ingrowth of fibrocollagenous tissue continues to fill the intervertebral disc space that has been vacated by the removal of the balloon device.

In summary, the present invention is a method and assembly which permits surgery for a disc herniation which is relatively non-invasive and which permits the patient a relatively short recovery time. An access port is created in the annulus portion of a herniated intervertebral disc. Using a guide tube through the access port, extruded pulp is removed from the herniated disc and the annulus may be annealed to aide healing. A balloon assembly is inserted through the guide tube into the nucleus portion of the disc for distraction or occupation of the intervertebral disc space. The balloon assembly may be utilized with a material which acts as a fibrocartiligenous seeding material to enhance the surgical outcome. The balloon assembly is filled with a physiologically compatible fluid to expand it for occupation and distraction purposes. The balloon assembly may have a nubbin, which is secured in the annulus of the disc to ensure that the balloon assembly stays in place and permit easy access to the balloon assembly for removal. The balloon assembly elements, such as the nubbin may be radiolucent to improve visualization of the assembly during insertion, expansion and removal processes. Further, the balloon assembly may be constructed of a dissolvable physiologically compatible composition which would dissolve over a specified period of time to provide support in the disc space at the time of insertion and to dissolve during and after the ingrowth of tissue. This latter structure would alleviate the need for the subsequent balloon assembly removal procedure.

As many changes are possible to the method and embodiments of the assemblies of this invention utilizing the teachings thereof, the descriptions above, and the accompanying drawing should be interpreted in the illustrative and not in the limited sense.

That which is claimed is:

1. In a method for treating a herniated intervertebral disc utilizing an endoscopic procedure, comprising the steps of:
    a) creating an access port in the annulus of the herniated disc;
    b) removing nucleus pulposus from the disc through said access port and creating a disc space;
    c) inserting and inflating a balloon structure in said disc space;
    d) allowing the growth of fibrocartilegenus tissue in said disc space; and
    e) removing said balloon structure between one month and three years and subsequent the ingrowth of said fibrocartilegenus tissue.

2. The method of claim 1, wherein the disc space and the access port in the annulus are treated prior to step c).

3. The method of claim 2, wherein a powdered hydroxyapatite cell culture material or a homologous tissue cell culture seeding is placed in the disc space and wherein the access port is annealed by means of laser irradiation after step b).

4. The method of claim 1, wherein said access port provided has a diameter between 2.0 mm and 6.0 mm and wherein said balloon structure occupies or distracts said disc space.

5. The method of claim 1, wherein said balloon structure includes a radiolucent material.

6. The method of claim 1, wherein said balloon structure provided comprises a flexible balloon member and a nubbin portion and further wherein a valve member is positioned in said nubbin member.

7. The method of claim 6, wherein said balloon structure is filled with a physiological fluid.

8. A method of treating a herniated intervertebral disc comprising:
    a) utilizing an endoscopic procedure and creating an access port having a diameter between 2.0 mm and 6.0 mm in the annulus of the herniated disc;
    b) removing the nucleus pulposus of said herniated disc to thereby reduce pressure caused by the herniation and thereby creating a disc space;
    c) annealing the inner surface of the annulus by means of laser irradiation;
    d) inserting a flexible balloon assembly through said annulus and into the disc space and inflating the balloon in the disc space;
    e) permitting fibrocartiligenous tissue to grow in the disc space; and
    f) removing the balloon from the disc space.

9. The method of claim 8, wherein the access port created has a diameter of approximately 2.5 to 3.5 mm.

10. The method of claim 8, wherein the flexible balloon has a nubbin and a valve in said nubbin and wherein the nubbin is placed within in the access port of the annulus of the affected intervertebral disc.

11. The method of claim 10, wherein at least a portion of said balloon assembly is radiolucent.

12. The method of claim 8, wherein a second endoscopic surgery procedure is performed to remove the balloon assembly.

13. The method of claim 8, wherein hydroxyapatite is infused into the intervertebral disc space prior to the balloon assembly placement, said hydroxyapatite to facilitate the ingrowth of tissue in the disc space.

14. The method of claim 8, wherein said endoscopic procedure includes incising the skin and passing an endoscopic guide tube therethrough.

15. The method of claim 14, wherein said guide tube is a long radiolucent needle-like probe having an internal diameter of approximately 2.5 millimeters.

16. The method of claim 14, wherein said endoscopic instrument is removed after the insertion of the balloon assembly and whereby the incision is closed by a suture, bonding agent or an adhesive bandage.

17. The method of claim 14, wherein an imaging technique is utilized to guide the endoscopic guide tube.

18. The method of claim 8, wherein said flexible balloon assembly is expanded with physiological normal saline.

19. The method of claim 8, wherein powdered hydroxyapatite, cell culture material or a homologous tissue cell culture seeding is placed in the disc space prior to the placement of the balloon assembly to facilitate the ingrowth of structural tissue.

20. The method of claim 8, wherein said flexible balloon assembly occupies or distracts the disc space.

21. The method of claim 8, wherein the balloon assembly is removed from the disc space between one month to three years after insertion.

22. The method of claim 21, wherein the balloon is deflated and removed via a guide tube and through the port in the annulus.

23. A method for treating a herniated intervertebral disc utilizing an endoscopic procedure, comprising the steps of:
   a) creating an access port in the annulus of the herniated disc;
   b) removing nucleus pulposus from the disc through said access port and creating a disc space;
   c) annealing said disc space and said access port by means of laser irradiation;
   d) placing a powdered hydroxyapatite cell culture material or a homologous tissue cell culture seeding in said disc space; and
   e) inserting and inflating a balloon structure in said disc space.

24. The method of claim 23, wherein said balloon structure is removed from said disc space subsequent the ingrowth of fibrocartilegenus tissue in said disc space.

25. The method of claim 23, wherein said balloon structure is inflated to occupy or distract said disc space.

26. The method of claim 23, wherein said balloon structure provided comprises a flexible balloon member and a nubbin portion and further wherein a valve member is positioned in said nubbin member and wherein said balloon structure is filled with a physiological fluid.

27. The method of claim 23 wherein said balloon structure includes a radiolucent material.

28. The method of claim 23, wherein said access port provided has a diameter between 2.0 mm and 6.0 mm and wherein said endoscopic procedure includes incising the skin and passing an endoscopic guide tube therethrough, wherein an imaging technique is utilized to guide the endoscopic guide tube and wherein a second endoscopic surgery procedure is performed to remove the balloon assembly.

29. The method of claim 23, wherein said balloon structure includes a radiolucent material.

30. A method for treating a herniated intervertebral disc utilizing an endoscopic procedure, comprising the steps of:
   a) creating an access port in the annulus of the herniated disc,
   b) removing nucleus pulposus from the disc through said access port and creating a disc space;
   c) inserting and inflating a balloon structure in said disc space, said balloon structure provided being comprised of a flexible balloon member and a nubbin portion having a valve member; and
   d) filling said balloon structure with a physiological fluid.

31. The method of claim 30, wherein said balloon structure is removed from said disc space subsequent the ingrowth of fibrocartilegenus tissue in said disc space.

32. The method of claim 30, annealing the disc space and the access port in the annulus by means of laser irradiation after step b) and placing a powdered hydroxyapatite cell culture material or a homologous tissue cell culture seeding in said disc space.

33. The method of claim 30, wherein said access port provided has a diameter between 2.0 mm and 6.0 mm and wherein said endoscopic procedure includes incising the skin and passing an endoscopic guide tube therethrough, wherein an imaging technique is utilized to guide the endoscopic guide tube and wherein a second endoscopic surgery procedure is preformed to remove the balloon assembly.

34. The method of claim 30, wherein said flexible balloon assembly is expanded with physiological normal saline.

35. The method of claim 30, wherein said flexible balloon assembly is inflated to occupy or distract the disc space.

* * * * *